(12) United States Patent
Jiang

(10) Patent No.: US 8,906,611 B2
(45) Date of Patent: *Dec. 9, 2014

(54) DEVICES AND METHODS FOR IMMOBILIZING NUCLEIC ACIDS

(75) Inventor: Wenlong Jiang, Madison, WI (US)

(73) Assignee: OpGen, Inc., Gaithersburg, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 13/190,947

(22) Filed: Jul. 26, 2011

(65) Prior Publication Data

US 2013/0029347 A1   Jan. 31, 2013

(51) Int. Cl.
| | |
|---|---|
| *C12Q 1/68* | (2006.01) |
| *C12M 1/00* | (2006.01) |
| *C12M 1/34* | (2006.01) |
| *C12N 15/74* | (2006.01) |
| *G01N 15/06* | (2006.01) |
| *G01N 21/00* | (2006.01) |
| *B01J 19/08* | (2006.01) |
| *B05B 5/025* | (2006.01) |
| *B01L 3/00* | (2006.01) |

(52) U.S. Cl.
CPC ....... *B01L 3/502761* (2013.01); *C12Q 2523/31* (2013.01); *B01L 2400/0427* (2013.01); *C12Q 1/689* (2013.01); *B01L 2200/0663* (2013.01); *C12Q 1/6825* (2013.01)
USPC ... 435/6.1; 435/283.1; 435/287.2; 435/288.5; 435/478; 422/68.1; 422/82.05; 427/457; 118/620

(58) Field of Classification Search
USPC ................. 435/6.1, 283.1, 287.2, 288.5, 478; 422/68.1, 82.05; 427/457; 118/620
See application file for complete search history.

(56) References Cited

U.S. PATENT DOCUMENTS

| | | | | |
|---|---|---|---|---|
| 5,720,928 | A | * | 2/1998 | Schwartz ...................... 422/186 |
| 2003/0027201 | A1 | | 2/2003 | Schwartz |
| 2005/0106596 | A1 | | 5/2005 | Skrzypczynski et al. |
| 2006/0081643 | A1 | * | 4/2006 | Haluzak et al. ................. 222/52 |
| 2009/0311713 | A1 | * | 12/2009 | Pollack et al. .................... 435/6 |

OTHER PUBLICATIONS

Chu-Jiang et al, Surface topography and character of γ-aminopropyltriethoxysilane and dodecyltrimethoxysilane films adsorbed on the silicon dioxide substrate via vapour phase deposition, 2006, J. Phys. D: Appl. Phys. 39, 4829-4837.*
Freiberg et al, The impact of transcriptome and proteome analyses on antibiotic drug discovery, 2004, Current Opinion in Microbiology, 7, 451-459.*
Kim et al, DC electric-field-induced DNA stretching for AFM and SNOM studies, 2002, Ultramicroscopy, 91, 139-149.*
Shukla et al, Optical Mapping Reveals a Large Genetic Inversion between Two Methicillin-Resistant *Staphylococcus aureus* Strains, 2009, Journal of Bacteriology, 191, 5717-5723.*
Kim et al. "Simple fabrication of hydrophillic nanochannels using the chemical bonding between activated ultrathin PDMS layer and cover glass by oxygen" Lab Chip; 2011; vol. 11; p. 348-353.
Kim et al. "Hydrophobic Recovery of Polydimethylsiloxane Elastomer Exposed to Partial Electrical Discharge" J. Colloid INterface Sci.; Jun. 15, 2000; vol. 226, No. 2; pp. 231-236.
Nimittrakoolchal et al. "Deposition of transparent, hydrophobic polydimethylsiloxane—nanocrystalline TiO2 hybrid films on glass substrate" Songklanakarin J. Sci. Technol.; Mar.-Apr. 2012; vol. 32, No. 2, p. 157-162.
Dimalanta et al. "A Microfluidic System for Large DNA Molecule Arrays" Anal. Chem.; 2004; vol. 76; p. 5293-5301.
Tegenfeldt et al. "Micro- and nanofluidics for DNA analysis". Anal. Bioanal. Chem.; 2004; vol. 378; p. 1678-1692.
International Search Report and Written Opinion for PCT/US12/48136, mailed Oct. 26, 2012.

\* cited by examiner

*Primary Examiner* — Narayan Bhat

(74) *Attorney, Agent, or Firm* — Brown Rudnick LLP; Thomas C. Meyers

(57) ABSTRACT

The present invention generally relates to devices and methods for immobilizing nucleic acids on a substrate. In certain embodiments, devices of the invention include a voltage source, and a substrate coupled to the voltage source, in which hydrophobicity of the substrate changes in response to an applied electric field and a surface of the substrate is coated with a substance that retains nucleic acids.

14 Claims, No Drawings

DEVICES AND METHODS FOR IMMOBILIZING NUCLEIC ACIDS

FIELD OF THE INVENTION

The present invention generally relates to devices and methods for immobilizing nucleic acids on a substrate.

BACKGROUND

Physical genomic mapping using restriction endonucleases can provide accurate information about the nucleic acid sequences of various organisms. Optical mapping can be used to produce ordered restriction maps that are visualized using fluorescence microscopy. In optical mapping, nucleic acids are digested by restriction enzymes on a glass surface. The nucleic acids are fixed and elongated on the surface to provide access to restriction sites for the enzymes. Generally, a microchannel is temporarily sealed to a charged glass substrate by mechanical placement, a small volume of nucleic acid solution is flowed into the resulting microchannels, excess nucleic acid solution is removed from the surface/channel interface, followed by the removal of the microchannel to continue processing for optical mapping protocols.

A problem with deposition techniques that use microchannels is that the manual intervention required significantly hinders development of high throughput optical mapping protocols. Further, standard microchannel protocols are not optimal with respect to scalability and automation for high-throughput optical mapping.

Previous attempts to automate the optical mapping process have relied on microfluidic chips that include vents, valves, and pumps. Those chips have many moving parts and have proved to be unreliable and inefficient for fluid movement during the optical mapping process.

There is a need for methods that provide a mechanism of delivering stretched individual nucleic acid molecules to a substrate for high throughput optical mapping.

SUMMARY

The present invention generally provides devices and methods that use electrowetting to control fluid flow for deposition and elongation of nucleic acids on a charged substrate. Electrowetting involves modifying the surface tension of liquids on a solid surface using a voltage. By applying a voltage, the wetting properties of a hydrophobic surface can be modified and the surface becomes increasingly hydrophilic (wettable). Devices and methods of the invention are driven by voltage, thus eliminating moving parts (e.g., vents, valves, and pumps), and also eliminating the need for bulk flow based nucleic acid deposition techniques and the need for microchannels. Methods of the invention allow for the automated immobilization and characterization of nucleic acids that have been fixed and elongated on a surface.

In certain aspects, devices of the invention include a voltage source, and a substrate coupled to the voltage source, in which hydrophobicity of the substrate changes in response to an applied electric field and a surface of the substrate is coated with a substance that retains nucleic acids. Exemplary substrates include a flow cell or a channel. An exemplary surface includes glass, preferably glass that is coated with silanes. The surface also includes a conductive material, such as metal. Devices of the invention may also include reservoirs that are fluidically coupled to the substrate.

Other aspects of the invention provide methods for elongating nucleic acids on a substrate. Methods of the invention include temporarily applying an electric field to temporarily decrease hydrophobicity of a charged substrate, thereby causing a sample fluid comprising a nucleic acid to temporarily flow onto the charged substrate, and maintaining the electric field for a time sufficient to allow the nucleic acid to interact with the charged substrate and become elongated and fixed on the substrate. The nucleic acid may be DNA or RNA and may have any origin, e.g., human or microorganism.

Other aspects of the invention provide methods for characterizing nucleic acids. Such methods include temporarily applying an electric field to temporarily decrease hydrophobicity of a charged substrate, thereby causing a sample fluid comprising a nucleic acid to temporarily flow onto the charged substrate, maintaining the electric field for a time sufficient to allow the nucleic acid to interact with the charged substrate and become elongated and fixed on the substrate so that the nucleic acid remains accessible for enzymatic reactions, intermittently re-applying the electric field to cause reagents to flow to and from the substrate to wash, enzymatically digest, and stain the nucleic acid to obtain one or more restriction digests of the nucleic acid, and imaging the restriction digests, thereby characterizing the nucleic acid. Methods of the invention may further include constructing an optical map from the restriction digests.

The nucleic acid may DNA or RNA and may have any origin, e.g., human or microorganism. In particular embodiments, the nucleic acid is from a microorganism, such as a bacterium. The bacterium may be any bacterium. In certain embodiments, the bacterium is a species of *E. coli* or *S. aureus*. The strain of *S. aureus* may be a community-acquired methicillin-resistant strain of *S. aureus* or a hospital-acquired methicillin-resistant strain of *S. aureus*. The nucleic acid may include substantially all genomic DNA of the bacterium. In certain embodiments, the nucleic acid includes a transcriptome of the bacterium.

DETAILED DESCRIPTION

In certain aspects, the invention provides devices for depositing and elongating nucleic acids on a charged substrate. Devices of the invention may include a voltage source and a substrate coupled to the voltage source, in which hydrophobicity of the substrate changes in response to an applied electric field and a surface of the substrate is coated with a substance that retains nucleic acids.

Devices of the invention utilize electrowetting to control movement of fluid. Electrowetting-on-dielectric microfluidics is based on the actuation of droplet volumes up to several microliters using the principle of modulating the interfacial tension between a liquid and an electrode coated with a dielectric layer. An electric field established in the dielectric layer creates an imbalance of interfacial tension if the electric field is applied to only one portion of the droplet on an array, which forces the droplet to move.

Devices of the invention are based on charge control manipulation at the solution/insulator interface of discrete droplets by applying voltage to a control electrode. Devices of the invention exhibits bilateral transport, are electrically isolated, use a gate electrode for charge-controlled transport, have a threshold voltage, and are a square-law device in the relation between droplet velocity and gate actuation voltage.

Further description of devices that utilize electrowetting to control fluid movement and methods of using electrowetting for fluid manipulation are shown for example in Fair (Microfluidics and Nanofluidics, 3:245-281, 2007); Fair et al. (IEEE Design & Test of Computers, 24:10-24, 2007); Song (Microfluidics and Nanofluidics, 7:75-89, 2009); Chakrabarty (IEEE Transactions on Computer-Aided Design of Integrated Circuits and Systems, 29:1001-1017, 2010); Pollack et al. (Applied Physics Letters, 77(11), 2000); Pollack et al. (Lab on a Chip, 2:96-101, 2002); Su et al. (Proc. IEEE International Test Conference, 1192-1200, 2003); Fair et al. ("Electrowetting-based On-Chip Sample Processing for Integrated Microfluidics", IEEE Inter. Electron Devices Meeting (IEDM), 2003); Ren et al. (Sensors and Actuators B (Chemical), B98:319-327, 2004); Fei et al. (IEEE Transactions on Computer-Aided Design of Integrated Circuits and Systems, 25:211-223, 2006); Pamula et al. (U.S. Pat. Nos. 6,911,132; 7,329,545; 7,439,014; and 7,569,129); Kolar et al. (U.S. Pat. No. 6,989,234); and Pollack et al. (U.S. Pat. No. 7,759,132). The content of each of the above is incorporated by reference herein in its entirety.

In certain embodiments, devices of the invention include a metal coated insulator that is about 1 to about 20 micrometers thick. The insulator is coated with a hydrophobic material at a thickness of about 0.1 to about 1 micrometer. Exemplary materials include Paralyene C and Teflon. These components are combined with a charged surface and held together by glue to build the device. The charged surface may be glass that is derivatized with silanes. The device further includes at least one solution port for connection to at least one fluid reservoir. The metal component of the device and the solution port are connected to a controllable voltage source.

The voltage source is coupled to a controller. The controller is used to set the voltage and the timing, allowing for devices of the invention to flow several solutions onto the charged surface at defined sequences and times. Electrowetting drives the movement of fluid onto the charged substrate.

Devices of the invention may be used to generate optical maps. Optical mapping is a single-molecule technique for production of ordered restriction maps from a single DNA molecule (Samad et al., *Genome Res.* 5:1-4, 1995). During some applications, individual fluorescently labeled DNA molecules are elongated and fixed on the surface using methods of the invention. The added endonuclease cuts the DNA at specific points, and the fragments are imaged. Id. Exemplary endonucleases include BglII, NcoI, XbaI, and BamHI. Exemplary combinations of restriction enzymes include:

| | | |
|---|---|---|
| AflII | ApaLI | BglII |
| AflII | BglII | NcoI |
| ApaLI | BglII | NdeI |
| AflII | BglII | MluI |
| AflII | BglII | PacI |
| AflII | MluI | NdeI |
| BglII | NcoI | NdeI |
| AflII | ApaLI | MluI |
| ApaLI | BglII | NcoI |
| AflII | ApaLI | BamHI |
| BglII | EcoRI | NcoI |
| BglII | NdeI | PacI |
| BglII | Bsu36I | NcoI |
| ApaLI | BglII | XbaI |
| ApaLI | MluI | NdeI |
| ApaLI | BamHI | NdeI |
| BglII | NcoI | XbaI |
| BglII | MluI | NcoI |
| BglII | NcoI | PacI |
| MluI | NcoI | NdeI |
| BamHI | NcoI | NdeI |
| BglII | PacI | XbaI |
| MluI | NdeI | PacI |
| Bsu36I | MluI | NcoI |
| ApaLI | BglII | NheI |
| BamHI | NdeI | PacI |
| BamHI | Bsu36I | NcoI |
| BglII | NcoI | PvuII |
| BglII | NcoI | NheI |
| BglII | NheI | PacI |

Restriction maps can be constructed based on the number of fragments resulting from the digest. Id. Generally, the final map is an average of fragment sizes derived from similar molecules. Id.

Optical mapping and related methods are described in U.S. Pat. Nos. 5,405,519, 5,599,664, 6,150,089, 6,147,198, 5,720, 928, 6,174,671, 6,294,136, 6,340,567, 6,448,012, 6,509,158, 6,610,256, and 6,713,263. All the cited patents are incorporated by reference herein in their entireties.

Optical Maps are constructed as described in Reslewic et al., Appl Environ Microbiol. 2005 September; 71 (9):5511-22, incorporated by reference herein. Briefly, individual chromosomal fragments from test organisms are immobilized on derivatized glass by virtue of electrostatic interactions between the negatively-charged DNA and the positively-charged surface, digested with one or more restriction endonuclease, stained with an intercalating dye such as YOYO-1 (Invitrogen) and positioned onto an automated fluorescent microscope for image analysis. Since the chromosomal fragments are immobilized, the restriction fragments produced by digestion with the restriction endonuclease remain attached to the glass and can be visualized by fluorescence microscopy, after staining with the intercalating dye. The size of each restriction fragment in a chromosomal DNA molecule is measured using image analysis software and identical restriction fragment patterns in different molecules are used to assemble ordered restriction maps covering the entire chromosome.

An exemplary protocol for using devices of the invention to generate an optical map is described herein. A sample containing nucleic acids is obtained. The sample may be a human tissue or body fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues.

A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, mammary fluid, urine, and cerebrospinal fluid (CSF), such as lumbar or ventricular CSF. A sample may also be a fine needle aspirate or biopsied tissue. A sample also may be media containing cells or biological material.

The sample may also be an environmental sample such as water, air, dirt, rock, etc. In other embodiments, the sample is a food sample.

Nucleic acid is then extracted from the sample. Methods of extracting nucleic acids and methods of purifying biological samples are known in the art. See for example, Maniatis et al., Molecular Cloning: A Laboratory Manual, Cold Spring Harbor, N.Y. (1982).

The process further involves capture and elongation of nucleic acid on a charged substrate. A solution containing the extracted nucleic acids is loaded into a first fluid reservoir and the reservoir is coupled to a solution port of the device. Due to the hydrophobicity of the surface of the device, the solution remains in the reservoir and does not flow onto the substrate.

The voltage source of the device is turned on, resulting in the hydrophobic surface becoming more hydrophilic, which causes the solution containing the nucleic acid to flowed from the first reservoir onto the charged substrate. The charged substrate can be composed of any material that is suitable for optical mapping and is compatible with nucleic acids. Exemplary materials include polymers, ceramics, glass, or metals. In a preferred embodiment, the surface is glass, such as a microscope slide. Because a net positive charge is require to capture/retain nucleic acids, the surface includes silanes to impart a net positive charge to the surface. Interaction between the nucleic acid in the solution and the charged substrate results in capture and elongation of the nucleic acid on the substrate.

After a sufficient time is allowed for the nucleic acid solution to interact with the charged substrate, the voltage is turned off and the solution returns to the reservoir because the surface changes from hydrophilic to hydrophobic. This process may optionally be repeated several time to ensure that a sufficient amount of nucleic acid has been fixed and elongated on the charged substrate.

After fixation and elongation of the nucleic acids on the charged substrate, the first fluid reservoir is disconnected from the device and a second fluid reservoir is connected to the device. The second fluid reservoir includes a buffer, such as TE buffer. The voltage is turned on, causing the TE buffer to flow from the second reservoir onto the charged substrate. The voltage is maintained for a time sufficient to rinse the substrate and remove nucleic acids that have not become fixed to the substrate. An exemplary amount of time is one minute. The voltage is then turned off, and the TE buffer returns to the second reservoir.

The second fluid reservoir is disconnected from the device and a third fluid reservoir is connected to the device. The third fluid reservoir includes a solution of restriction enzymes in a suitable buffer. Enzymes for use with optical mapping are discussed above. The voltage is turned on, causing the digestion solution to flow from the third reservoir onto the charged substrate. The voltage is maintained for a time sufficient to allow the restriction enzymes to interact with the nucleic acids and digest the nucleic acids on the substrate. Since nucleic acids have charge, the digestion of the nucleic acids may be manipulated by the applied voltage. After a sufficient time has elapsed, the voltage is turned off and the digestion solution returns to the third reservoir.

After digestion, the third fluid reservoir is disconnected from the device and a fourth fluid reservoir is connected to the device. The fourth fluid reservoir includes a nucleic acid staining solution, such as YOYO-1. The voltage is turned on, causing the staining solution to flow from the fourth reservoir onto the charged substrate. The voltage is maintained for a time sufficient to allow the staining solution to interact with the digested nucleic acids. After a sufficient time has elapsed, the voltage is turned off and the staining solution returns to the fourth reservoir. The substrate is now ready for image analysis.

Restriction mapping, e.g., optical mapping, can be used in a variety of applications. For example, the methods featured herein can be used to determine a property, e.g., physical and/or chemical property, e.g., size, length, restriction map, weight, mass, sequence, conformational or structural change, pKa change, distribution, viscosity, rates of relaxation of a labeled and/or non-labeled molecule, e.g., an amplicon (e.g., PCR product), of a portion of a genome (e.g., a chromosome), or of an entire genome.

Optical mapping can also be used to identify various organisms, e.g., viruses and prions, and various microorganisms, e.g., bacteria, protists, and fungi, whose genetic information is stored as DNA or RNA by correlating the restriction map of a nucleic acid of an organism with a restriction map database. Such identification methods can be used in diagnosing a disease or disorder. Methods of identifying organisms by restriction mapping are described, e.g., in a U.S. patent application Ser. No. 12/120,586, filed on May 14, 2008, incorporated herein by reference. The methods featured herein can also be used in other diagnostic applications, for example, imaging specific loci or genetic regions for individuals or populations to help identify specific diseases or disorders. Other uses of the methods will be apparent to those skilled in the art.

The methods described herein can be used in a variety of settings, e.g., to identify an organism in a human or a non-human subject, in food, in environmental sources (e.g., food, water, air), and in industrial settings. The featured methods also include methods of diagnosing a disease or disorder in a subject, e.g., a human or a non-human subject, and treating the subject based on the diagnosis. The method includes: obtaining a sample comprising an organism from the subject; imaging a nucleic acid from the organism; obtaining a restriction map of said nucleic acid; identifying the organism by correlating the restriction map of said nucleic acid with a restriction map database; and correlating the identity of the organism with the disease or disorder.

As discussed above, various organisms can be identified by the methods discussed herein and therefore various diseases and disorders can be diagnosed by the present methods. The organism can be, e.g., a cause, a contributor, and/or a symptom of the disease or disorder. In one embodiment, more than one organism can be identified by the methods described herein, and a combination of the organisms present can lead to diagnosis. Skilled practitioners would be able to correlate the identity of an organism with a disease or disorder. For example, the following is a non-exhaustive list of some diseases and bacteria known to cause them: tetanus—*Clostridium tetani*; tuberculosis—*Mycobacterium tuberculosis*; meningitis×*Neisseria meningitidis*; botulism—*Clostridium botulinum*; bacterial dysentry—*Shigella dysenteriae*; lyme disease—*Borrelia burgdorferi*; gasteroenteritis—*E. coli* and/or *Campylobacter* spp.; food poisoning—*Clostridium perfringens, Bacillus cereus, Salmonella enteriditis*, and/or *Staphylococcus aureus*. These and other diseases and disorders can be diagnosed by the methods described herein.

Once a disease or disorder is diagnosed, a decision about treating the subject can be made, e.g., by a medical provider or a veterinarian. Treating the subject can involve administering a drug or a combination of drugs to ameliorate the disease or disorder to which the identified organism is contributing or of which the identified organism is a cause. Amelioration of the disease or disorder can include reduction in the symptoms of the disease or disorder. The drug administered to the subject can include any chemical substance that affects the processes of the mind or body, e.g., an antibody and/or a small molecule, The drug can be administered in the form of a composition, e.g., a composition comprising the drug and a pharmaceutically acceptable carrier. The composition can be in a form suitable for, e.g., intravenous, oral, topical, intramuscular, intradermal, subcutaneous, and anal administration. Suitable pharmaceutical carriers include, e.g., sterile saline, physiological buffer solutions and the like. The pharmaceutical compositions may be additionally formulated to control the release of the active ingredients or prolong their presence in the patient's system. Numerous suitable drug delivery systems are known for this purpose and include, e.g., hydrogels, hydroxmethylcellulose, microcapsules, liposomes, microemulsions, microspheres, and the like. Treating the subject can also include chemotherapy and radiation therapy.

Incorporation By Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for elongating a nucleic acid, the method comprising:
    providing a device comprising a voltage source coupled to a controller, a fluid reservoir, and a charged substrate operably associated with the voltage source and the fluid reservoir, wherein a hydrophobicity of the charged substrate changes in response to an applied electric field and the substrate is coated with a substance that retains the nucleic acid;
    temporarily applying an electric field via the controller to temporarily decrease the hydrophobicity of the charged substrate, thereby causing a sample fluid comprising the nucleic acid in the fluid reservoir to temporarily flow from the reservoir onto the charged substrate;
    maintaining the electric field via the controller so that the sample fluid remains on the charged substrate for a time sufficient to allow a sufficient amount of the nucleic acid to interact with the charged substrate and become elongated and fixed on the substrate; and
    turning-off the electric field via the controller to thereby increase the hydrophobicity of the charged substrate and cause the sample fluid to flow back into the reservoir while the elongated and fixed nucleic acid remains on the charged substrate.

2. The method according to claim 1, wherein the nucleic acid is DNA.

3. The method according to claim 1, wherein the nucleic acid is from a microorganism.

4. The method according to claim 3, wherein the microorganism is a bacterium.

5. A method for characterizing a nucleic acid, the method comprising:
    providing a device comprising a voltage source coupled to a controller, one or more fluid reservoirs, and a charged substrate operably associated with the voltage source and the one or more reservoirs, wherein a hydrophobicity of the substrate changes in response to an applied electric field and the charged substrate is coated with a substance that retains nucleic acids;
    temporarily applying an electric field via the controller to temporarily decrease the hydrophobicity of the charged substrate, thereby causing a sample fluid comprising the nucleic acid to temporarily flow from the fluid reservoir onto the charged substrate, wherein the fluid reservoir is fluidically coupled to the device;
    maintaining the electric field via the controller so that the sample fluid remains on the charged substrate for a time sufficient to allow a sufficient amount of the nucleic acid to interact with the charged substrate and become elongated and fixed on the substrate so that the nucleic acid remains accessible for enzymatic reactions;
    turning-off the electric field via the controller to thereby increase the hydrophobicity of the charged substrate and cause the sample fluid to flow back into the reservoir while the elongated and fixed nucleic acid remains on the charged substrate;
    intermittently re-applying the electric field via the controller to thereby intermittently decrease the hydrophobicity of the charged substrate to cause reagents to flow to and from the substrate to wash, enzymatically digest, and stain the nucleic acid to obtain one or more restriction digests of the nucleic acid, wherein the reagents are in individual fluid reservoirs, the individual fluid reservoirs are fluidically coupled to the device, and turning-off the electric field via the controller increases the hydrophobicity of the charged substrate and causes the reagents to flow back into the respective individual reservoir; and
    imaging the restriction digests, thereby characterizing the nucleic acid.

6. The method according to claim 5, further comprising constructing an optical map from the restriction digests.

7. The method according to claim 5, wherein the nucleic acid is DNA.

8. The method according to claim 5, wherein the nucleic acid is from a microorganism.

9. The method according to claim 8, wherein the microorganism is a bacterium.

10. The method according to claim 9, wherein the nucleic acid comprises substantially all genomic DNA of the bacterium.

11. The method according to claim 9, wherein the nucleic acid comprises a transcriptome of the bacterium.

12. The method according to claim 9, wherein the bacterium is at least one species selected from the group consisting of *Escherichia coli* (*E. coli*) and *Staphylococcus aureus* (*S. aureus*).

13. The method according to claim 12, wherein the *S. aureus* is a community-acquired methicillin-resistant strain of *S. aureus*.

14. The method according to claim 12, wherein the *S. aureus* is a hospital-acquired methicillin-resistant strain of *S. aureus*.

* * * * *